United States Patent [19]

Hüsler et al.

[11] Patent Number: 5,616,787
[45] Date of Patent: Apr. 1, 1997

[54] PROCESS FOR THE PREPARATION OF ALKYLATED AROMATIC CARBOXYLIC ACIDS AND ACYL HALIDES

[75] Inventors: Rinaldo Hüsler, Wünnewil; Ivan Orban, Basel; Martin Holer, Magden, all of Switzerland

[73] Assignee: Ciba-Geigy Corporation, Tarrytown, N.Y.

[21] Appl. No.: 541,006

[22] Filed: Oct. 11, 1995

[30] Foreign Application Priority Data

Oct. 13, 1994 [CH] Switzerland .............. 3078/94

[51] Int. Cl.$^6$ .................................................. C07C 51/58
[52] U.S. Cl. ............................................ 562/423; 562/861
[58] Field of Search .................................. 562/423, 861

[56] References Cited

U.S. PATENT DOCUMENTS

| | | | |
|---|---|---|---|
| 1,866,717 | 7/1932 | Meyer et al. ............... | 562/423 |
| 3,138,626 | 6/1964 | Calfee ........................ | 260/448 |
| 3,520,926 | 7/1970 | Bollag et al. ............... | 260/558 |
| 4,730,083 | 3/1988 | Pastor et al. ............... | 562/423 |

FOREIGN PATENT DOCUMENTS

| | | |
|---|---|---|
| 619204 | 3/1976 | Switzerland . |
| 307223 | 3/1929 | United Kingdom . |

OTHER PUBLICATIONS

James F. Norris et al., Journal Amer. Chem. Soc., vol. 62, pp. 1428–1432 1940.

Hiroshi Sugimoto et al., Journal of Oranometallic Chem. Soc., 266, pp. C44–C46 (1984).

Friedel–Crafts and Related Reactions, George A. Olah, III, Part 2, Interscience Publishers, pp. 121–122 & 1269–1270, (1964).

Derw. Abst. 77512x/42 of CH 619,204 27 Sep. 1976.

*Primary Examiner*—Paul J. Killos
*Attorney, Agent, or Firm*—Michele A. Kovaleski; David R. Crichton

[57] ABSTRACT

The invention relates to a process for the preparation of polyalkylated aromatic carboxylic acids of formula I

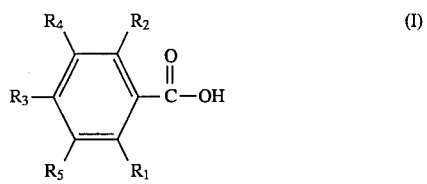

wherein $R_1$, $R_2$, $R_3$, $R_4$ and $R_5$ are each independently of one another hydrogen, $C_1$–$C_{20}$alkyl, halogen or $C_5$–$C_8$cycloalkyl, with the proviso that at least two of the substituents $R_1$, $R_2$, $R_3$, $R_4$ or $R_5$ are alkyl and/or cycloalkyl, by reacting corresponding aromatic hydrocarbons with carbon dioxide, which reaction is carried out observing special ratios of temperature and pressure. The invention furthermore relates to a one-pot process for the preparation of the corresponding acyl halides.

19 Claims, No Drawings

PROCESS FOR THE PREPARATION OF ALKYLATED AROMATIC CARBOXYLIC ACIDS AND ACYL HALIDES

The present invention relates to a process for the preparation of alkylated aromatic carboxylic acids from alkylated aromatic hydrocarbons, as well as to a process for the preparation of the corresponding acyl halides.

Methods for the preparation of aromatic sterically hindered carboxylic acids and the corresponding acyl halides are already known in the art. Org. Synth. Coll. Vol. 2, 583 (1943), inter alia, describes the reaction of mesitylene with carbon monoxide in the presence of $AlCl_3$ and CuCl, the carboxylic acid being obtained via the aldehyde stage by treatment with $HNO_3$ (Friedel-Crafts formylation according to Gattermann-Koch). A further possibility is the halocarbonylation with oxalyl chloride described in Org. Synth. Coll. Vol. 5, 706 (1973). In the Gattermann-Adams synthesis, an aromatic hydrocarbon is first reacted with zinc cyanide in the presence of $AlCl_3$ to give the imide hydrochloride, which is then hydrolysed to the aldehyde and converted into the corresponding carboxylic acid by treatment with $HNO_3$ (Org. Synth. Coll. Vol. 3, 549 (1955)). The reaction of aromatic hydrocarbons with $\alpha,\alpha$-dihalo ethers and subsequent hydrolysis to the aldehyde is known from Org. Synth. Coll. Vol. 5, 49 (1973). EP-A-46 194 (1982) discloses a process wherein an aromatic hydrocarbon is first acetylated and the reaction product is then converted into the corresponding carboxylic acid by the haloform reaction. In the Gattermann amide synthesis, the carbamide compound is prepared from an aromatic hydrocarbon by reaction with the corresponding acyl chlorides in the presence of $AlCl_3$ and then hydrolysed to the carboxylic acid (Annalen 244,29,55 (1888); Chem. Ber. 32, 1116 (1899)). In Chem. Ber. 97,472 (1964) and Chem. Ber. 18,873 (1885), aromatic carboxylic acids are obtained by reacting aromatic hydrocarbons with aromatic isocyanates in the presence of $AlCl_3$ and subsequent hydrolysis with $H_3PO_4$. In the cyanate synthesis, an aromatic hydrocarbon is reacted with sodium cyanate in the presence of $AlCl_3$ to the amide and then converted with sodium nitrite in acetic and sulfuric acid to the carboxylic acid (Angew. Chem. 61, 183 (1949); DE-A-584142 (1932); Houben-Weyl, Vol. 8, 381 and 432; Chem. Ber. 32, 1118 (1889)). The carboxylation of Grignard compounds with subsequent hydrolysis to the carboxylic acid is described in Org. Synth. Coll. Vol. 3, 551–555 (1955). In U.S. Pat. No. 3,187,057 (1965), aromatic carboxylic acids are prepared by Friedel-Crafts synthesis using carbon tetrachloride instead of phosgene. A further possible synthesis is the carbamidation of aromatic hydrocarbons with urethane and subsequent hydrolysis to the acid (Synthesis 1981,977). J. Am. Chem. Soc. 80, 6393 (1958) describes the preparation of aromatic carboxylic acids by hydrolysis of esters which are obtained via the Baeyer-Villiger oxidation from the corresponding ketones. In the Cannizarro reaction, aromatic aldehydes disproportionate in basic medium into the corresponding carboxylic acids and alcohols (T. A. Geissmann, Org. Reactions, II, 94 (1944), J. Wiley & Sons, Inc. New York, London). A general suvey of Friedel-Crafts reactions is given in George A. Olah, Friedel-Crafts and Related Reactions, Vol. 3, Part 2, 1257–1269 (1964). GB-A-307 223 discloses the carboxylation of aromatic hydrocarbons with carbon dioxide using aluminium chloride as catalyst. In this reaction, the educts are reacted under pressure in the temperature range from 50° to 200° C. Yuzo Fujiwara et al. carry out the same reaction using palladium acetate as catalyst (J. Organomet. Chem., 266, C44–C46 (1984)). In J. Am. Chem. Soc. 62, 1428 (1940), James. F. Norris and John E. Wood disclose the reaction of aromatic hydrocarbons with $CO_2$ using aluminium bromide as catalyst. The reactions are all carried out in an autoclave under elevated pressure.

Although a great number of methods of synthesis are known, as has been outlined above, they are unsatisfactory when used for the preparation of alkylated sterically hindered aromatic carboxylic acids. During the acid hydrolysis of amide or ester intermediates, for example, decarboxylation of the carboxylic acid obtained readily occurs. In many reactions, including also reactions with carbon dioxide under pressure and at elevated temperature, substantial amounts of undesirable by-products are obtained, e.g. the corresponding benzophenone derivatives. These reactions are also not advantageous in view of the complicated apparatus and investment in technical resources required for carrying them out under high pressure.

Alkylated aromatic carboxylic acids and acyl halides, in particular acyl chlorides, have numerous utilities, inter alia as intermediates for the synthesis of e.g. adhesives. Such carboxylic acids and acyl halides are also important intermediates in the synthesis of photoinitiator compounds such as monoacylphosphine oxides (see e.g. EP-A-7 508), bisacylphosphine oxides (see e.g. EP-A-184 095), benzophenone derivatives (see e.g. EP-A-209 831) or thermal catalysts such as N-acylimidazoles (see e.g. EP-A-124 482). Accordingly, there is a need for simple and economic processes for the preparation of these starting materials.

It has now been found that, when certain process conditions are observed, the desired carboxylic acids are mainly obtained and only minor amounts of the unwanted benzophenone derivatives.

Accordingly, the invention relates to a process for the preparation of carboxylic acids of formula I

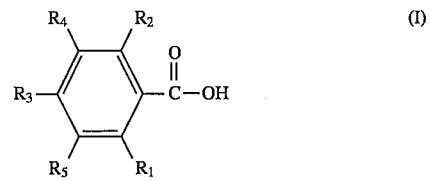

wherein $R_1$, $R_2$, $R_3$, $R_4$ and $R_5$ are each independently of one another hydrogen, $C_1$–$C_{20}$alkyl, halogen and $C_5$–$C_8$cycloalkyl, with the proviso that at least two of the substituents $R_1$, $R_2$, $R_3$, $R_4$ and $R_5$ are alkyl and/or cycloalkyl, by reacting aromatic hydrocarbons of formula (II)

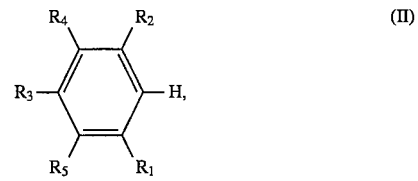

wherein $R_1$, $R_2$, $R_3$, $R_4$ and $R_5$ have the meanings given above, in the presence of a Friedel-Crafts catalyst with carbon dioxide, and hydrolysing the complexes obtained to the corresponding carboxylic acid, which process comprises carrying out the carboxylation reaction under a maximum pressure of 10 bar and in the temperature range from –20° C. to +40° C.

$R_1$, $R_2$, $R_3$, $R_4$ and $R_5$, defined as $C_1$–$C_{20}$alkyl can be linear or branched and are typically methyl, ethyl, propyl, isopropyl, butyl, isobutyl, sec-butyl, tert-butyl, pentyl, isopentyl, hexyl, heptyl, octyl, nonyl, decyl, dodecyl, octadecyl or eicosyl. It is preferred to use $C_1$–$C_{18}$alkyl, typically $C_1$–$C_{12}$alkyl or $C_1$–$C_8$alkyl and, preferably, $C_1$–$C_4$alkyl.

$R_1$, $R_2$, $R_3$, $R_4$ and $R_5$ are preferably methyl.

$R_1$, $R_2$, $R_3$, $R_4$ and $R_5$ defined as $C_5$–$C_8$cycloalkyl are cyclopentyl, cyclohexyl, cycloheptyl and cyclooctyl, preferably cyclopentyl and cyclohexyl, most preferably cyclohexyl.

Halogen is typically chloro, bromo and iodo, preferably chloro. Accordingly, halide is chloride, bromide and iodide, preferably chloride.

The catalysts used for Friedel-Crafts reactions are usually those described in George A. Olah, Friedel-Crafts and Related Reactions, Vol. I, 201 and 284–90 (1963). Aluminium trihalides such as $AlBr_3$ and $AlCl_3$ are particularly suitable for the novel process. $AlCl_3$ is preferred.

A preferred process is that wherein the carboxylation reaction is carried out using $AlCl_3$ or $AlBr_3$ as catalyst. A particularly preferred process comprises carrying out the carboxylation reaction using $AlCl_3$ as catalyst.

The novel process can be carried out without a solvent. Thus, for example, the aromatic hydrocarbon of formula II itself, when liquid, can be used as solvent, in which case it is used in excess. It will be readily understood that the novel process can also be carried out in inert solvents. Suitable solvents are, for example, the solvents described in George A. Olah, Friedel-Crafts and Related Reactions, Vol. 1, 298–302 (1963). The choice of the respective solvent depends on the solubility of the educts and catalysts. Typical examples of solvents which may be used in the novel process are halogenated hydrocarbons such as chlorobenzene, dichlorobenzene, carbon tetrachloride, dichloromethane, tetrachloroethylene, bromobenzene, aromatic hydrocarbon derivatives such as nitrobenzene, dinitrobenzene, benzene and toluene, saturated aliphatic hydrocarbons such as pentane, hexane, heptane and the mixtures of isomers thereof, petroleum ether or cyclohexane, or further solvents, typically carbon disulfide, nitroalkanes such as nitromethane, diethyl ether, dimethyl sulfoxide or tetramethylene sulfone.

Benzene, toluene, chlorobenzene and heptane are preferred solvents.

In a special embodiment of the novel process the carboxylation reaction is carried out in a solvent, preferably toluene, chlorobenzene or heptane.

The novel process comprises carrying out the carboxylation reaction at low temperature and under normal pressure or slight overpressure. It is preferred not to apply overpressure in the novel process.

The $CO_2$ gas is passed into, or over, the reaction solution under a maximum pressure of 10 bar, i.e. typically 1–10 bar, 1 bar corresponding to c. 760 torr. Accordingly, carrying out the reaction at 1 bar means working under normal pressure without applying overpressure.

Pressures in the range from 1 to 5 bar are particularly suitable for the novel process. In the novel process the reaction can also be carried out under slight underpressure, typically by evacuating the apparatus and then releasing the pressure with $CO_2$ gas, the gas pressure being kept below 1 bar.

A preferred process is that wherein the carboxylation reaction is carried out without applying overpressure.

Also of interest is a process wherein the carboxylation reaction is carried out under a pressure of 1–5 bar.

As already mentioned above, in the novel process it is not absolutely necessary to introduce the $CO_2$ gas into the reaction solution. It is normally sufficient to introduce the $CO_2$ gas into the reaction vessel over the surface of the reaction mixture, which has the advantage the inlet tube cannot get blocked.

Customary operations, such as stirring the reaction mixture, are advantageous.

A preferred process is that wherein the $CO_2$ gas is passed into the reaction vessel over the surface of the stirred reaction mixture.

An essential feature of the novel process is temperature control, as the benzophenone compounds of the respective carboxylic acids are mainly obtained as unwanted by-products at too high temperatures even if $CO_2$ is introduced under normal pressure.

The novel process is desirably carried out in the temperature range from −20° C. to +40° C., more particularly from 0° C. to 35° C., preferably at room temperature, typically from 18° C. to 25° C.

While carrying out the exothermic reaction, the reaction mixture is conveniently cooled by conventional methods to maintain the above-mentioned temperatures.

A particularly preferred process is that wherein the carboxylation reaction is carried out at 0° C. to 35° C.

Also of interest is a process which comprises carrying out the carboxylation reaction at room temperature.

The reaction time depends on the pressure applied. The higher the pressure, the shorter the reaction times. However, the amount of undersirable by-products increases when the pressure is too high.

In the novel process the compound of formula II and the catalyst should desirably be present in at least equal stoichiometric amounts, i.e. the molar ratio of catalyst and aromatic hydrocarbon should ideally be 1:1. However, it is expedient to add one of the components in excess. A convenient molar ratio of catalyst to aromatic hydrocarbon is typically from 2:1 to 1:10, preferably from 2:1 to 1:5.

However, if the aromatic hydrocarbon of formula II is also used as solvent, then the hydrocarbon may also be used in any excess. However, if the catalyst is added in excess, then it should desirably be added in not more than the double amount.

If, for example, the carboxylation reaction is carried out without addition of a solvent, then e.g. the hydrocarbon of formula II is added in excess. If, however, a solvent is used in the novel process, then it is expedient to use approximately equal molar amount of catalyst and hydrocarbon of formula II.

A preferred process is that wherein the molar ratio of catalyst to aromatic hydrocarbon of formula II is from 2:1 to 1:10.

The carboxylic acid itself does not form direct during the reaction, but, as those skilled in the art know, complexes of catalyst and acid form first. The free acid is obtained from these complexes by addition of water. In addition to water, it is useful to add also hydrochloric acid during hydrolysis.

The $C_2$ is conveniently added to the reaction mixture in gaseous form, typically by introducing it from pressure vessels or by evaporating solid $C_2$.

A particularly preferred process is that wherein $R_1$ is $C_1$–$C_8$alkyl, $R_2$ is hydrogen or $C_1$–$C_4$alkyl, $R_3$ is hydrogen or $C_1$–$C_8$alkyl, $R_4$ is hydrogen, chloro, bromo, cyclohexyl or $C_1$–$C_8$alkyl, and $R_5$ is hydrogen or methyl.

Also of interest is a process wherein $R_1$, $R_2$ and $R_3$ are $C_1$–$C_8$alkyl and $R_4$ and $R_5$ are hydrogen.

Another preferred process is that wherein $R_1$, $R_2$ and $R_3$ are methyl.

A process wherein $R_1$, $R_2$, $R_3$, $R_4$ and $R_5$ are methyl is also of interest.

The aromatic hydrocarbons of formula II to be used as starting materials in the novel process are known, and some are commercially available. They can also be prepared by the alkylation processes commonly employed in the art and which are known to the skilled person. Such processes are described, inter alia, by Michael Novak et al. in Journal of Chemical Education, Vol. 70, No. 6, A150–154 (June 1993).

If the aromatic hydrocarbons of formula II are prepared by one of the processes known in the art, then they can also be used in the novel process without any prior purification. The novel process can typically also be carried out direct without isolating the intermediate of formula II in the reaction solution obtained in the preparation of said intermediate. The use of the novel process is restricted to the carboxylation of polyalkylated or polycycloalkylated aromatic hydrocarbons. Accordingly, the novel process is not suitable for the carboxylation of alkoxy-substituted and hydroxy-substituted aromatic hydrocarbons.

With the novel process it is also possible to obtain carboxylic acids halogenated in the aromatic nucleus by using aromatic hydrocarbons halogenated in the aromatic nucleus as educts. However, it is more expedient to first prepare the corresponding halogen-free carboxylic acids and then to introduce the halogen substituent by halogenating the aromatic nucleus.

The compounds of formula I can be converted into the corresponding acyl halides by processes conventionally employed in the state of the art. Org. Syntheses Coll. Vol. 3 (1955), 555–6 describes, inter alia, the reaction with thionyl chloride. Further reactions may be found in Houben-Weyl, Methoden der Organischen Chemie, Vol. VIII, pages 463–469 (1952), Georg Thieme Verlag, Stuttgart, and Houben-Weyl, Vol. E5, pages 593–600 (1985), Georg Thieme Verlag, Stuttgart.

It is also possible to convert the carboxylic acids into the corresponding halides, preferably chlorides, directly after the novel process for the preparation of the carboxylic acids with or without prior isolation thereof.

The invention also relates to a process for the preparation of acyl halides of formula Ia

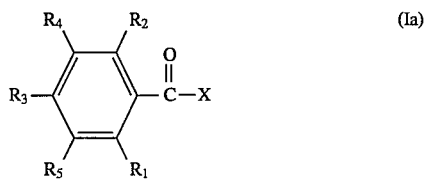

wherein $R_1$, $R_2$, $R_3$, $R_4$ and $R_5$ are each independently of one another hydrogen, $C_1$–$C_{20}$alkyl, halogen or $C_5$–$C_8$cycloalkyl, and X is halogen, with the proviso that at least two of the substituents $R_1$, $R_2$, $R_3$, $R_4$ or $R_5$ are alkyl and/or cycloalkyl, by reacting aromatic hydrocarbons of formula (II)

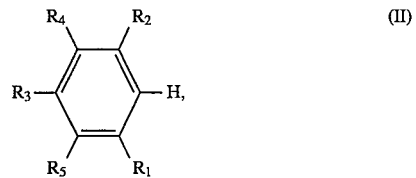

wherein $R_1$, $R_2$, $R_3$, $R_4$ and $R_5$ have the meanings given above, in the presence of a Friedel-Crafts catalyst with carbon dioxide, and hydrolising the resulting complexes to the corresponding carboxylic acid of formula I

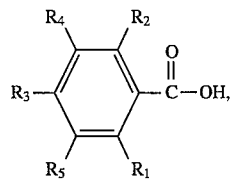

and then, after optional conversion of the acid into an alkali metal salt, reacting said acid or salt to an acyl halide of formula Ia by reaction with a halogenating agent, which comprises carrying out the carboxylation reaction under a maximum pressure of 10 bar and in the temperature range from −20° C. to +40° C., and carrying out the halogenation with or without prior isolation of the carboxylic acid of formula I.

X defined as halogen is Cl, Br or I, more particularly Cl or Br, preferably Cl.

The above-described process can also be carried out as a one-pot reaction. This means that the carboxylic acid obtained in the novel process is not isolated and characterised as such, but is reacted directly in the subsequent reaction step to the corresponding halide, preferably chloride. After obtaining the carboxylic acid in this manner, only water and the aluminium salts obtained are removed from the reaction mixture. The residual carboxylic acid remains dissolved in the excess aromatic hydrocarbon, if used as solvent, or in the corresponding solvent. It is expedient to remove any traces of water by distillation before carrying out the halogenation.

It will be readily understood that in the novel process the carboxylic acid can also be first isolated and then halogenated.

An interesting process is that wherein the halogenation is carried out without isolating the carboxylic acid intermediate.

Suitable halogenating agents will be found, inter alia, in Houben-Weyl, Methoden der Organischen Chemie, Vol. VIII, pages 463–469 and 475–476 (1952), Georg Thieme Verlag, Stuttgart, and in Houben-Weyl, Vol. E5, pages 593–600 (1985), Georg Thieme Verlag, Stuttgart.

Suitable chlorinating agents for converting carboxylic acids into acyl chlorides are typically inorganic acid chlorides such as thionyl chloride, phosphorus trichloride, phosphorus pentachloride or phosgene, or oxalyl chloride. Thionyl chloride is preferred. It is cenovenient to use an excess of thionyl chloride. To increase the action of thionyl chloride, catalytic amounts of pyridine or dimethyl formamide, preferably dimethyl formamide, are usefully added during the reaction.

The bromides are typically prepared by using phosphorus tribromide or phosphorus pentabromide. The iodides are conveniently obtained by transhalogenation of the corresponding acyl chlorides.

A preferred process for the preparation of acyl halides of formula Ia is that wherein X is Cl or Br, preferably Cl.

Another interesting process for the preparation of acyl chlorides, wherein X is Cl, comprises using thionyl chloride as halogenating agent.

It is also possible to convert the carboxylic acids obained in the novel process into their alkali metal salts and to react these with phosphoroxy chloride, thionyl chloride, phosphorus trichloride or phosphorus pentachloride to the corresponding acyl chloride by separating the acyl chloride in liquid or solid form. The salt is then obtained by the addition of, for example, sodium hydroxide or sodium carbonate, and is then isolated, purified and dried by methods known to the person skilled in the art before it is halogenated as described above. The halogenation of sodium salts of carboxylic acids is described, inter alia, in Houben-Weyl, Methoden der Organischen Chemie, Vol. VIII, pages 466–467 (1952), Georg Thieme Verlag, Stuttgart.

After removing the excess reactants, in particular the water, from the first reaction step by distillation, a solvent may be added before halogenating the resultant carboxylic acid of formula I. Solvents which are suitable for the reaction of the carboxylic acids to the corresponding acyl halides, preferably acyl chlorides, are those having a boiling point which is not too high (readily distillable), typically toluene, xylene, mesitylene, chlorobenzene and the like.

As already mentioned at the outset, the compounds obtainable by the novel process are important starting materials for the preparation of photoinitiator compounds. Mixtures of isomers and mixtures of carboxylic acids can also be obtained in the novel process (see Example 17). It is expedient not to separate these mixtures, but to convert them direct into the halides, preferably chlorides, and to react them to photoinitiators. The product mixtures can be used, for example, direct for the preparation of bisacylphosphine oxide photoinitiators. Bisacylphosphine oxide mixtures (typically also initiators containing two differently substituted benzoyl groups) are then thus obtained. These initiator mixtures have lowered melting ranges and hence increased solubility in the compositions to be polymerised. Accordingly, they can be more readily incorporated into the substrates and do not recrystallise in the substrate.

In contrast to most of the processes known in the state of the art, which are often carried out via aldehyde, or other, intermediates, the novel process affords the possibility of preparing the corresponding carboxylic acid direct from the aromatic hydrocarbon without any further intermediate steps. The carboxylic acids and acyl halides obtainable by the novel process are, as illustrated above, important intermediates for the synthesis of photoinitiator compounds. The novel process has the advantage that these intermediates can be prepared economically, without complicated apparatus and expenditure of technological resources, and without excessive formation of unwanted by-products.

The following Examples illustrate the invention in more detail. In the Examples, as well as throughout the remainder of the description and in the claims, part and percentages are by weight, unless otherwise stated.

All compounds obtained are confirmed by thin-layer chromatography, gas chromatography (GC) and $^1$H-nuclear magnetic resonance spectroscopy ($^1$H-NMR).

I) Preparation of the Educts

EXAMPLE A

Preparation of 1-octyl-2,4,6-trimethylbenzene

A 750 ml flask is charged with 6.7 g (50 mmol) of anhydrous aluminium chloride and 120.2 g (1 mol) of mesitylene. 148.7 g (1 mol) of 1-chloroctane are added dropwise to this mixture over 2 h at room temperature. HCl gas slowly evolves. The dark orange emulsion is stirred for c. 30 h at room temperature and then poured into water and extracted with toluene. The organic phase is isolated and concentrated on a rotary evaporator. The resultant oil is fractionated under vacuum to give, at 88°–92° C. and 1.8 mbar, 80.6 g of the title product as a colourless liquid. Gas chromatography (GC) and $^1$H-NMR spectrum analysis show that mono-n-octylmesitylene is obtained in 90% purity. The distillation residue contains mainly dioctylmesitylene.

Elemental analysis: $C_{17}H_{28}$

| calcd.: | C: | 91.84% | found: | C: | 91.67% |
|---|---|---|---|---|---|
|  | H: | 8.16% |  | H: | 8.25% |

EXAMPLE B

Preparation of 1-octyl-3,5-dimethylbenzene and isomers

In general accordance with the method of Example A, but by solely distilling off the solvent without fractionation and after stirring for 27 h at room temperature, 198.5 g of an mixture of isomers of the title product are obtained as a colourless liquid from 106.2 g (1 mol) of m-xylene, 148.7 g (1 mol) of 1-chloroctane and 6.7 g (50 mmol) of anhydrous aluminium chloride. $^1$H-NMR analysis shows the following four main components: 1-n-octyl-3,5-dimethylbenzene, 1-(methylhept-1-yl)-3,5-dimethylbenzene, 1-(ethylhex-1-yl)-3,5-dimethylbenzene and 1-(propylpent- 1-yl)-3,5-dimethylbenzene.

Elemental analysis: $C_{16}-H_{26}$

| calcd.: | C: | 87.99% | found: | C: | 87.80% |
|---|---|---|---|---|---|
|  | H: | 12.00% |  | H: | 12.16% |

EXAMPLE C

Preparation of 1-sec-butyl-2,4,6-trimethylbenzene

In general accordance with the method of Example A and after stirring for 6 hours at room temperature and distillation at 56° C./5 mbar, 290.5 g of the title product are obtained as a colourless liquid in 90% purity (GC) from 240.4 g (2 mol) of mesitylene, 185.2 g (2 mol) of 2-chlorobutane and 13.3 g (0.1 mol) of anhydrous aluminium chloride.

Elemental analysis: $C_{13}H_{20}$

| calcd.: | C: | 88.57% | found: | C: | 88.54% |
|---|---|---|---|---|---|
|  | H: | 11.43% |  | H: | 11.38% |

EXAMPLE D

Preparation of 1-sec-butyl-3,5-dimethylbenzene

In general accordance with the method of Example A, but by solely distilling off the solvent without fractionation and after stirring for 20 h at room temperature, 64.4 g of the title product are obtained as a colourless liquid in 95% purity (GC) from 63.7 g (0.6 mol) of m-xylene, 46.3 g (0.5 mol) of 2-chlorobutane and 6.7 g (50 mmol) of anhydrous aluminium.

Elemental analysis: $C_{12}H_{18}$

| calcd.: | C: | 88.82% | found: | C: | 88.79% |
|---|---|---|---|---|---|
|  | H: | 11.18% |  | H: | 11.15% |

EXAMPLE E

Preparation of 1-cyclohexyl-2,4,5-trimethylbenzene

A 200 ml flask is charged with 3.3 g (0.25 mmol) of anhydrous aluminium chloride and 60.1 g (0.50 mol) of mesitylene. To this mixture are then added dropwise 45.2 g (0.55 mol) of cyclohexene over, 2.5 hours at room temperature. The resultant solution is stirred for 2 hours at room temperature, poured into water and extracted with toluene. The organic phase is isolated and concentrated on a rotary evaporator. The resultant oil is fractionated under vacuum to give, at 80° C. and 5 mbar, 83.1 g of the title product as a colourless oil. GC and $^1$H-NMR spectrum analysis show that 1-cyclohexyl-2,4,5-trimethylbenzene is obtained in 97.7% purity.

Elemental analysis: $C_{15}H_{22}$

| calcd.: | C: | 89.40% | found: | C: | 88.89% |
|---|---|---|---|---|---|
| | H: | 10.96% | | H: | 11.09% |

II) Preparation of the Aromatic Carboxylic Acids

Example 1

Preparation of 2,4,6-trimethylbenzoic acid

A 1.5 l sulfonation flask is charged with 400 g (3.0 mol) of anhydrous aluminium chloride and 432.7 g (3.6 mol) of pure mesitylene. Into this mixture is then passed, with stirring, $CO_2$ gas at 20° C.–30° C. under normal pressure. No HCl gas evolves during this reaction. Owing to the exothermic reaction, the reaction mixture must be cooled to maintain the temperature. After c. 6 hours, $CO_2$ uptake is complete. The resultant suspension is poured onto ice and hydrochloric acid solution and then diluted with hexane. The crystalline product is isolated by filtration and washed with water and hexane. The crystals are dried under vacuum at 50° C., to give 167.0 g of white crystals (c. 68% of theory) having a melting point of 154.0°–156.1° C. Thin-layer chromatography and gas chromatography confirm the purity of the crystals, and no further by-products can be detected. The mother liquor is concentrated to give 10.3 g of white crystals (c. 4% of theory) containing, however, in addition to 2,4,6-trimethylbenzoic acid, 13% of hexamethylbenzophenone as by-product (GC).

It is possible to recover 262 g of mesitylene by distillation.

Elemental analysis: $C_{10}H_{12}O$

| calcd.: | C: | 73.15% | found: | C: | 73.07% |
|---|---|---|---|---|---|
| | H: | 7.37% | | H: | 7.36% |

EXAMPLES 2–13

The compounds of Examples 2–13 are obtained according to the process described in Example 1. The compounds as well as their educts and physical data are listed in Table 1 below. The compounds are characterised as crude products without prior recrystallisation. Exceptions are marked in the Table. In some Examples a solvent is used. These Examples and the solvents used are also listed in the Table.

TABLE 1

| Ex. | Product | Educt | Melting point: [°C.] | Elemental analysis [%] calcd./found | | |
|---|---|---|---|---|---|---|
| | | | | C | H | halogen |
| 2 | 2,4-dimethyl-benzoic acid | 1,3-dimethyl-benzene | 123.5–127.5 | 71.98 71.98 | 6.71 6.82 | — |
| 3 | 2,3,4-trimethyl-benzoic acid | 1,2,3-triethyl-benzene | 130–135 | 73.15 73.14 | 7.37 7.42 | — |
| 4 | 2,4,5-trimethyl-benzoic acid | 1,2,4-trimethyl-benzene | 148–150 | 73.15 72.86 | 7.37 7.37 | — |
| 5 | 2,3,4,6-tetra-methylbenzoic acid | 1,2,3,5-tetra-methylbenzene | 166–168.8 | 74.13 74.01 | 7.92 7.96 | — |
| 6 | 2,3,5,6-tetra-methylbenzoic acid* | 1,2,4,5-tetra-methylbenzene | 115–125*[1] | 74.13 74.10 | 7.92 8.00 | — |
| 7 | 2,3,4,5,6-pentamethyl-benzoic acid | 1,2,3,4,5-pentamethyl-benzene | 212–213.5*[2] | 74.97 74.99 | 8.39 8.49 | — |
| 8 | 2-tert-butyl-3,6-dimethylbenzoic acid | 1-tert-butyl-3,5-dimethyl-benzene | 137–140.3 | 75.69 75.63 | 8.79 8.88 | — |
| 9 | 2,4,6-triethyl-benzoic acid | 1,3,5-triethyl-benzene | 115.8–117.2*[3] | 75.69 75.77 | 8.79 8.87 | — |
| 10 | 2,4,6-triiso-propylbenzoic acid | 1,3,5-triiso-propylbenzene | 184–188 | 77.38 77.38 | 9.74 9.77 | — |
| 11 | 2,4-diethyl-6-methylbenzoic acid | 1,3-diethyl-5-methylbenzene | 91–93 | 74.97 74.99 | 8.39 8.36 | — |
| 12 | 3-chloro-2,4,6-trimethylbenzoic acid | 2-chloro-1,3,5-trimethyl-benzene | 146–146.5 | 60.46 60.43 | 5.58 5.69 | 17.85 17.81 |
| 13 | 3-bromo-2,4,6-trimethylbenzoic acid | 2-bromo-1,3,5-trimethyl-benzene | 166–166.5*[2] | 49.41 49.44 | 4.56 4.77 | 32.87 32.92 |

*Toluene was used as solvent in the carboxylation reaction
*[1]Extracted with sodium hydroxide solution

TABLE 1-continued

| | | Melting | Elemental analysis [%] calcd./found | | |
|---|---|---|---|---|---|
| Ex. Product | Educt | point: [°C.] | C | H | halogen |

*[2] Recrystallised from ethanol
*[3] Recrystallised from hexane

EXAMPLE 14

Preparation of 1-sec-butyl-3,5-dimethylbenzene and of 2- and 4-sec-butyl-2,6-dimethylbenzoic Acid Therefrom Without Isolation of the Intermediate A 750 ml flask is charged with 13.3 g (100 mmol) of anhydrous aluminium chloride and 127.4 g (1.2 mol) of m-xylene. 92.6 g (1 mol) of 2-chlorobutane are added dropwise to this mixture over 1.5 h at 18°–20° C., and the mixture is then stirred for c. 23 h at 22° C. GC analysis shows that c. 15% of m-xylene, 85% of trialkylbenzene and less than 1% of tetraalkylbenzene are obtained. Without any further working up, 133.3 g (1 mol) of aluminium chloride are added. With stirring, $CO_2$ gas is then passed over the suspension over c. 14 h at room temperature. The yellowish orange emulsion is then poured onto ice/water and the organic phase is diluted with ether and separated. The ether phase is extracted twice with 10% sodium hydroxide solution. The sodium hydroxide solution is diluted with ether and, with cooling, acidified with concentrated hydrochloric acid. The aqueous phase is separated and the ether phase is then dried over $MgSO_4$, isolated by filtration and concentrated on a rotary evaporator to give 46.3 g of a colourless oil, which crystallises after a few days. The crystals have a melting point of 52°–60° C. GC and $^1$H-NMR analysis show that the crystals are a mixture of 54% of 4-sec-butyl-2,6-dimethylbenzoic acid and 46% of. 2-sec-butyl-4,6-dimethylbenzoic acid.

Elemental analysis: $C_{13}H_{18}O_2$

| calcd.: | C: | 75.69% | found: | C: | 75.67% |
|---|---|---|---|---|---|
| | H: | 8.79% | | H: | 8.75% |

It is possible to obtain educts and intermediates from the ether phase which has been extracted with sodium hydroxide solution.

EXAMPLE 15

Preparation of 2,4,6-trimethyl-3-n-octylbenzoic acid and isomers

A 350 ml flask is charged with 54.7 g (410 mmol) nhydrous aluminium chloride and 96.0 g of 1-octyl-2,4,6-trimethylbenzene (90%; of Example A). With stirring, $CO_2$ gas is passed into the reaction mixture at room temperature over c. 30 h. The black emulsion is then poured onto ice. The benzoic acid derivative is extracted from the organic phase with 10% sodium hydroxide solution, acidified with hydrochloric acid and extracted with ether. The ether phase is concentrated and dried over $MgSO_4$, to give 18.7 g of a pale yellow oil consisting 90% of the title product. The other components are 4% of an isomer and 6% of tetramethyl derivative. It is possible to recover 78.2 g of educt which can be recycled.

Elemental analysis: $C_{18}H_{28}O_2$

| calcd.: | C: | 78.21% | found.: | C: | 78.30% |
|---|---|---|---|---|---|
| | H: | 10.21% | | H: | 10.22% |

EXAMPLE 16

Preparation of 3-sec-butyl-2,4,6-trimethylbenzoic acid

A 750 ml flask is charged with 213.3 g (1.6 mol) of anhydrous aluminium chloride and 282.1 g of 1-sec-butyl-2,4,6-trimethylbenzene (90%; of Example C). With stirring, $CO_2$ gas is passed over the reaction mixture over c. 48 h at room temperature. The reddish brown emulsion is then poured onto ice. The benzoic acid derivative is then extracted from the organic phase with 10% sodium hydroxide solution, acidified with hydrochloric acid and extracted again with ether. The ether phase is concentrated, to give 44.2 g of moist crystals. These moist crystals are then added to hexane, isolated by filtration, washed and dried, to give 11.9 g of white crystals consisting 60% of 2,4,6-trimethylbenzoic acid and 40% of tetramethylbenzoic acid (GC and $^1$H-NMR analysis). It is possible to obtain 31.4 g of a pale yellow oil from the hexane solution which, according $^1$H-NMR spectrum and GC analysis, consists of a mixture of the title product and trimethylbenzoic acid (in about equal molar proportion). It is possible to recover unreacted educts from the organic phase. The oil can be separated by column chromatography. However, it is expedient to use it without separation for the preparation of photoinitiators.

EXAMPLE 17

Preparation of 4,6-dimethyl-2-octylbenzoic acid and 2,6-dimethyl-4-octylbenzoic acid (mixture of isomers)

A 750 ml flask is charged with 120 g (0.9 mol) of anhydrous aluminium chloride and 195.6 g of 1-octyl-3,5-dimethylbenzene (mixture of isomers of Example B). With stirring, $CO_2$ gas is passed over the mixture over 48 h at room temperature. The orange emulsion then turns dark red. The reaction mixture is poured onto ice, and the benzoic acid derivative is extracted from the organic phase with 10% sodium hydroxide solution. The three layers that form are separated. After acidification with hydrochloric acid and extraction with ether, the lowest layer gives 1 g of crystals which, according to GC analysis, are a mixture of trimethylbenzoic acid by-products. The middle layer is diluted with ether and acidified with concentrated hydrochloric acid. The ether phase is concentrated, to give 46.6 g of a yellow oil. Using a flash column (petroleum ether/ethyl acetate 5:1), 17.7 g of educt are then removed from this crude product. GC and $^1$H-NMR spectrum analysis show that the acid fraction, 26.4 g of a yellow oil, consists 62% of 4,6-dimethyl-2-octylbenzoic acid and 38% of 2,6-dimethyl-4- octylbenzoic acid. The octyl group is also isomerised: 7% of the products contain the 1-octyl group (=n-octyl), 64% of the products contain the 2-octyl group (=1-methylhept-1-yl) and 29% of the products contain the 3-octyl (=1-ethylhex-1-yl) and 4-octyl group (=1-propylpent-1-yl).
Elemental analysis: $C_{17}H_{26}O_2$

| calcd.: | C: | 77.82% | found: | C: | 77.73% |
|---|---|---|---|---|---|
| | H: | 9.99% | | H: | 10.15% |

EXAMPLE 18

Preparation of 3-cyclohexyl-2,5,6-trimethylbenzoic acid

A 350 ml flask is charged with 44.0 g (0.33 mol) of aluminium chloride and 80.9 g (0.40 mol) of 1-cyclohexyl-2,4,5-trimethylbenzene (97.7%; of Example E). With stirring, $CO_2$ gas is passed over the reaction mixture over c. 17 hours at room temperature. The dark brown solution is then diluted with 200 ml of toluene and poured onto ice. The two phases are separated and the organic phase is extracted with 10% sodium hydroxide solution. The basic aqueous phase is acidified with hydrochloric acid and extracted with toluene. The toluene phase is concentrated, giving 12.3 g of crystals. These crystals are recrystallised repeatedly from petroleum ether and then from hexane ethyl acetate. The purified crystals have a melting point of 170°–172° C. $^1$H-NMR analysis confirms this structure.
Elemental analysis: $C_{16}H_{22}O_2$

| calcd.: | C: | 78.01% | found: | C: | 77.92% |
|---|---|---|---|---|---|
| | H: | 9.00% | | H: | 8.96% |

EXAMPLE 19

Preparation of 2,4,6-trimethylbenzoic acid, Using Chlorobenzene as Solvent

A 2.5 l sulfonation flask is flushed with nitrogen and charged with 400 g (3.0 mol) of anhydrous aluminium chloride, 432.7 g (3.6 mol) of mesitylene and 433g of chlorobenzene. With stirring, $CO_2$ gas is passed over the suspension under normal pressure, while keeping the temperature at 20°–26° C. by gentle cooling. No HCl gas evolves during this reaction. After 7 h the resultant emulsion is poured onto ice and hydrochloric acid and then diluted with hexane. The suspension is filtered and the crystals are washed with water and hexane. The crystals are dried under vacuum at 70° C., to give 143.9 g (58% of theory) of white crystals having a melting point of 153.7°–155.5° C. Fractional concentration of the mother liquor and filtration to give a further 27.1 g (11% of theory) of white crystals (melting point 153°–154.7° C.). GC analysis confirms that neither of the two crystal fractions contains any further hexamethylbenzophenone.

EXAMPLE 20

Preparation of 2,4,6-trimethylbenzoic acid, using aluminium tribromide as catalyst A 350 ml flask is flushed with nitrogen and charged with 100 g (374 mmol) of anhydrous aluminium tribromide (under heptane), and 54.1 g (450 mmol) of mesitylene are then added. With stirring, $CO_2$ gas is then passed into the flask under normal pressure, while keeping the temperature at 20°–30° C. by gentle cooling. After 2 hours, the emulsion is poured onto ice and hydrochloric acid and diluted with heptane. The suspension is filtered and washed with water and heptane. The crystals are dried under vacuum at 50° C., to give 17.9 g (58% of theory) of white crystals having a melting point of 152°–154.5° C. Fractional concentration of the mother liquor gives a further 1.3 g (4% of theory) of white crystals (melting point 151°–53° C.). GC analysis confirms that neither of the two crystal fractions contains any further hexamethylbenzophenone.
Elemental analysis: $C_{10}H_{12}O_2$

| calcd.: | C: | 73.15% | found: | C: | 72.96% |
|---|---|---|---|---|---|
| | H: | 7.37% | | H: | 7.55% |

III) Preparation of the aromatic acyl chlorides

EXAMPLE 21

Preparation of 2,4,6-trimethylbenzoyl Chloride Without Isolating the Carboxylic Acid Intermediate A 1 l flask is charged with 400 g (3 mol) of anhydrous aluminium chloride and 432.7 g (3.6 mol) of mesitylene. The flask is evacuated and the pressure is then released with $CO_2$ gas. The suspension is stirred at 18°–22° C., while $CO_2$ gas is passed in over c. 3 hours under normal pressure. The apparatus is then closed and the pressure is increased to 1.5 bar by introducing $CO_2$ gas. After 5 hours, the $CO_2$ uptake is complete. A total of 2 mol of $CO_2$ gas are taken up. After releasing the pressure in the apparatus, the resultant suspension is poured onto ice and hydrochloric acid solution. The mixture is then diluted with 350 g of mesitylene and heated to c. 80° C. to dissolve the mesitylenecarboxylic acid. The aqueous phase is separated at c. 80° C. and the organic phase is washed with water. Residual traces of water are removed by concentrating the solution under normal pressure. 830 g of organic reaction solution are thus obtained which are used in the next step without further purification. 460 g of mesitylene are distilled off at 88°–100° C. under vacuum, and 1.1 g of dimethyl formamide are added to the residue. With stirring, 165 g (1.4 mol) of thionyl chloride are added dropwise to the mixture over 3 hours at 50° C., and subsequently the mixture is allowed to react further for c. 1 hour at 80° C. until the evolution of gas is complete. First the excess thionyl chloride (temperature in the vessel up to 115° C./7 mbar) and then unreacted mesityline (85° C. distillation temperature/7 mbar)) are removed by vacuum distillation. The title product then distills at up to 100° C. distillation temperature/7 mbar (the temperature in the vessel increases to 120° C.), to give 196 g of 2,4,6-trimethylbenzoyl chloride as a colourless oil having a content of 99% (=71% of theory).
Elemental analysis: $C_{10}H_{11}ClO$

| calcd.: | C: | 65.76% | found: | C: | 65.85% |
|---|---|---|---|---|---|
| | H: | 6.07% | | H: | 5.49% |
| | Cl: | 19.41% | | Cl: | 19.11% |

IV) Synthesis of a Photoinitiator (Use Example)

EXAMPLE 22

Synthesis of bis(2,4,6-trimethylbenzoyl)isobutylphosphine oxide 140.6 ml (0.225 mol; 1.6M) of butyllithium are added dropwise over 30 min under nitrogen to a solution consisting of 31.9 ml (0.225 mol) of diisopropylamine in 80 ml of tetrahydrofuran. This solution is added dropwise over 90 min at −30° C. to a solution of 41.1 g (0.225 mol) of 2,4,6-trimethylbenzoyl chloride and 12 ml (0.102 mol) of isobutylphosphine in 200 ml of tetrahydrofuran. After stirring for 2 h at −30° C., the yellow solution is allowed to warm to room temperature and is then washed once with water. The organic phase is dried over magnesium sulfate, filtered and concentrated on a rotary evaporator. The residue is dissolved in 200 ml of toluene, and 11.6 g (0.102 mol) of 30% hydrogen peroxide are added. The reaction solution is stirred for 2 h, washed first with water, then with saturated sodium hydrogen carbonate solution, dried over magnesium sulfate, subjected to filtration, and then concentrated on a rotary evaporator. Crystallisation from hexane gives 27.8 g (68.5% of theory) of the above compound as a yellow powder, melting point 85°–86° C.

| Elemental analysis: | calcd.: | C: 72.34% | found: | C: 72.13% |
| --- | --- | --- | --- | --- |
| | | H: 7.84% | | H: 7.94% |

What is claimed is:

1. A process for the preparation of a carboxylic acid of formula I

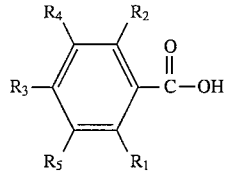

wherein $R_1$, $R_2$, $R_3$, $R_4$ and $R_5$ are each independently of one another hydrogen, $C_1$–$C_{20}$alkyl, halogen and $C_5$–$C_8$cycloalkyl, with the proviso that at least two of the substituents $R_1$, $R_2$, $R_3$, $R_4$ and $R_5$ are alkyl and/or cycloalkyl, by reacting an aromatic hydrocarbon of formula (II)

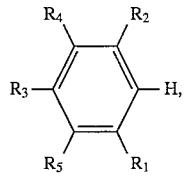

wherein $R_1$, $R_2$, $R_3$, $R_4$ and $R_5$ have the meanings given above, in the presence of a Friedel-Crafts catalyst with carbon dioxide and hydrolysing the complexes obtained to the corresponding carboxylic acid, which process comprises carrying out the carboxylation reaction under a maximum pressure of 10 bar and in the temperature range from −20° C. to +40° C.

2. A process according to claim 1, wherein the carboxylation reaction is carried out without applying overpressure.

3. A process according to claim 1, wherein the carboxylation reaction is carried out under a pressure of 1 to 5 bar.

4. A process according to claim 1, wherein the carboxylation reaction is carried out at 0 to 35° C.

5. A process according to claim 4, wherein the carboxylation reaction is carried out at room temperature.

6. A process according to claim 1, wherein the $CO_2$ gas is passed into the reaction vessel over the surface of the stirred reaction mixture.

7. A process according to claim 1, wherein the carboxylation reaction is carried out in a solvent.

8. A process according to claim 1, wherein the carboxylation reaction is carried out in toluene, chlorbenzene or hexane.

9. A process according to claim 1, wherein the carboxylation reaction is carried out using $AlCl_3$ or $AlBr3$ as catalyst.

10. A process according to claim 9, wherein the carboxylation reaction is carried out using $AlCl_3$ as catalyst.

11. A process according to claim 1, wherein the molar ratio of catalyst to aromatic hydrocarbon of formula II is from 2:1 to 1:10.

12. A process according to claim 1, wherein $R_1$ is $C_1$–$C_8$alkyl, $R_2$ is hydrogen or $C_1$–$C_4$alkyl, $R_3$ is hydrogen or $C_1$–$C_8$alkyl, $R_4$ is hydrogen, chloro, bromo, cyclohexyl or $C_1$–$C_8$alkyl, and $R_5$ is hydrogen or methyl.

13. A process according to claim 1, wherein $R_1$, $R_2$ and $R_3$ are $C_1$–$C_8$alkyl, and $R_4$ and $R_5$ are hydrogen.

14. A process according to claim 13, wherein $R_1$, $R_2$ and $R_3$ are methyl.

15. A process according to claim 1, wherein $R_1$, $R_2$, $R_3$, $R_4$ and $R_5$ are methyl.

16. A process for the preparation of an acyl halide of formula Ia

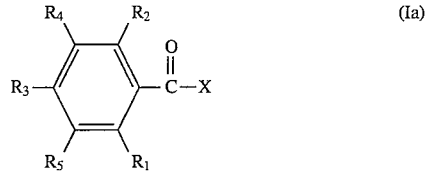

wherein $R_1$, $R_2$, $R_3$, $R_4$ and $R_5$ are each independently of one another hydrogen, $C_1$–$C_{20}$alkyl, halogen or $C_5$–$C_8$cycloalkyl, and X is halogen, with the proviso that at least two of the substituents $R_1$, $R_2$, $R_3$, $R_4$ or $R_5$ are alkyl and/or cycloalkyl, by reacting an aromatic hydrocarbon of formula (II)

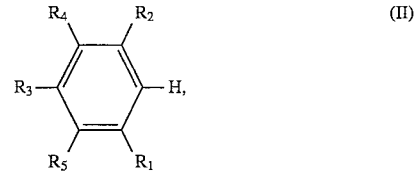

wherein $R_1$, $R_2$, $R_3$, $R_4$ and $R_5$ have the meanings given above, in the presence of a Friedel-Crafts catalyst with carbon dioxide and hydrolysing the resulting complex to the corresponding carboxylic acid of formula I

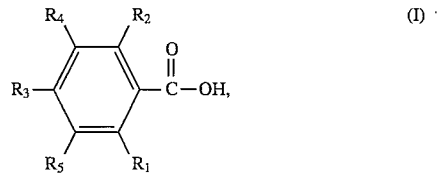

and then, after optional conversion of the acid into an alkali metal salt, reacting said acid or salt to an acyl halide of formula Ia by reaction with a halogenating agent, which comprises carrying out the carboxylation reaction under a maximum pressure of 10 bar and in the temperature range from −20° C. to +40° C. and carrying out the halogenation with or without prior isolation of the carboxylic acid of formula I.

17. A process according to claim 16, wherein X is Cl or Br.

18. A process according to claim 16, wherein X is Cl, and thionyl chloride is used as halogenating agent.

19. A process according to claim 16, wherein the halogenation is carried out without isolating the carboxylic acid intermediate.

* * * * *